United States Patent [19]
Hulfish

[11] Patent Number: 5,195,506
[45] Date of Patent: Mar. 23, 1993

[54] SURGICAL RETRACTOR FOR PUNCTURE OPERATION

[75] Inventor: Douglas A. Hulfish, Arlington Heights, Ill.

[73] Assignee: Life Medical Products, Inc., River Forest, Ill.

[21] Appl. No.: 779,299

[22] Filed: Oct. 18, 1991

[51] Int. Cl.⁵ .............................................. A61B 17/02
[52] U.S. Cl. ......................................... 128/20; 128/4; 606/198
[58] Field of Search ........................... 128/20, 17, 6, 4; 606/191, 198, 205, 206

[56] References Cited

U.S. PATENT DOCUMENTS

| | | | |
|---|---|---|---|
| 3,316,912 | 5/1967 | Whitaker | 606/191 X |
| 4,000,743 | 1/1977 | Weaver | 606/191 X |
| 4,190,042 | 2/1980 | Sinnreich | 128/20 |
| 4,654,028 | 3/1987 | Suma | 606/198 X |
| 4,909,789 | 3/1990 | Taguchi et al. | 606/198 X |

FOREIGN PATENT DOCUMENTS

| | | | |
|---|---|---|---|
| 246086 | 11/1987 | European Pat. Off. | 128/20 |
| 1333316 | 8/1987 | U.S.S.R. | 128/20 |

Primary Examiner—Robert Bahr
Assistant Examiner—Karen Ann Richard
Attorney, Agent, or Firm—Laff, Whitesel, Conte & Saret

[57] ABSTRACT

A surgical retractor is for use when extended through a trocar sleeve. The retractor has a pair of telescoping tubes. The inner one of the retractor tubes has a number of fingers which may be spread into a fan shape, and then articulated to select a position between 180° and 90° relative to the length of the tubes. For insertion and retraction into and out of the trocar sleeve, the fingers may be pulled into a compact configuration.

10 Claims, 2 Drawing Sheets

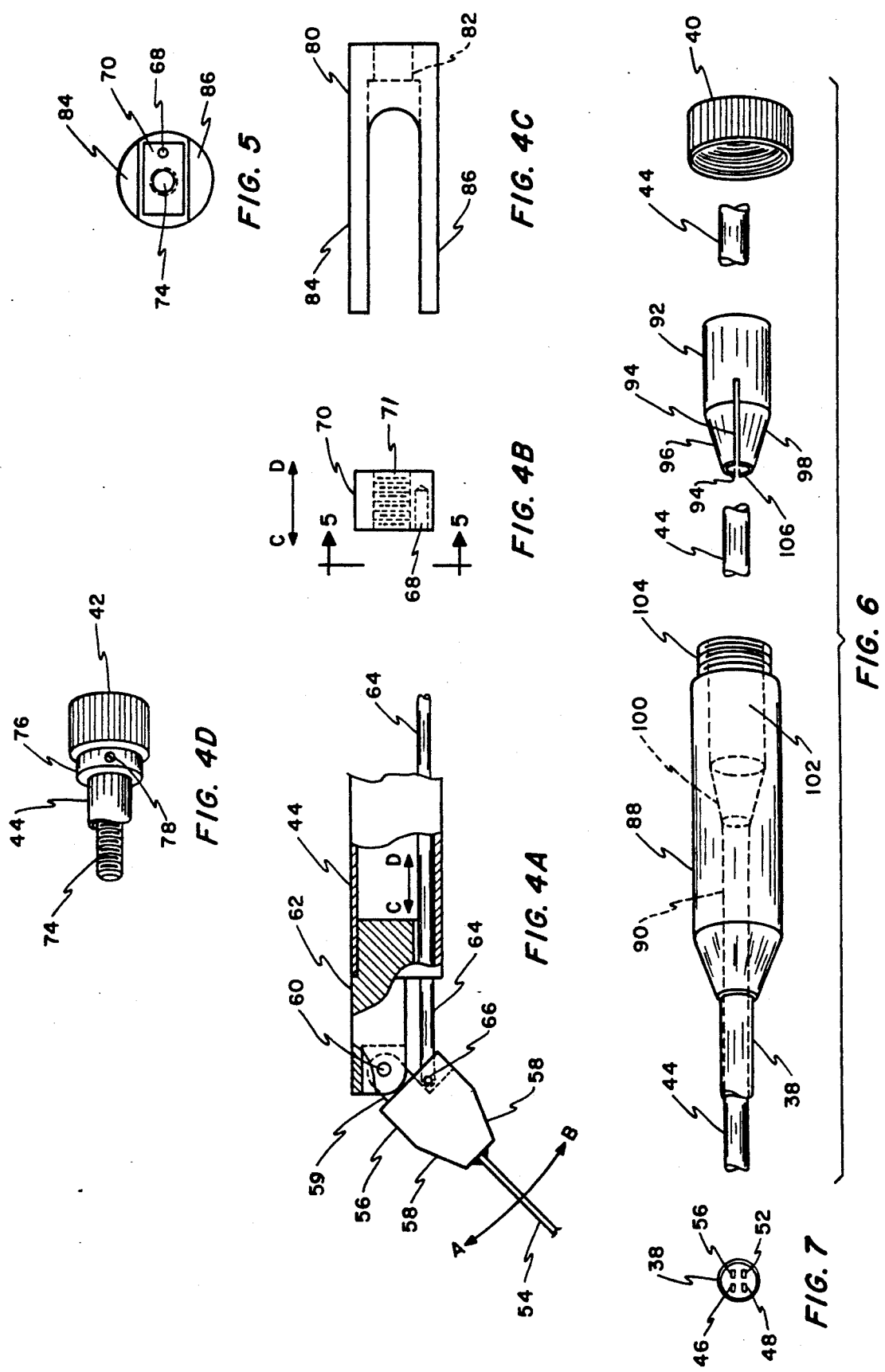

SURGICAL RETRACTOR FOR PUNCTURE OPERATION

This invention relates to surgical retractors and more particularly to retractors for insertion into a human body via a trocar sleeve.

Modern surgical procedures are being greatly simplified. Among other things, instead of extensively cutting and then retracting the surrounding tissue to provide a gaping wound, the modern trend is to provide a number of punctures into the human body with an insertion of a trocar sleeve through each puncture wound. Usually, all of the trocar sleeves are directed toward the point inside the body where the surgery actually is to be performed. Laparoscopes may be inserted into selected ones of the trocar sleeves, especially to return signals which are used to display an image on a video monitor, especially while the surgery is being performed. During surgery, there is a need to gently move tissue so that the point of surgery may be exposed to the laparoscope or surgical tools.

When the surgeon is ready to perform an operation, various tools are inserted through the trocar sleeves in order to do the cutting, pinching off, etc. which is the actual surgery that prompted the procedure. As this happens, it is again desirable to retract, move or otherwise mechanically act upon the tissue and expose the area within the body where the surgery is to be performed.

With all of these and different needs, it is necessary to insert, use, locate, relocate, etc. the retractors. The retractors should be small enough to be inserted through the trocar sleeve, which means that the outside diameter of the retractor should be a tube which is no more than in the order of approximately 0.350 to 0.400 of an inch, for example. The inside parts of the retractor must be manipulated by parts small enough to be packaged within the smaller inside diameter of the retractor tube. Moreover, the entire retractor must be made in a way which may be completely sanitized. It should be made of a light weight material so that less weight is placed upon the human tissue surrounding and supporting the trocar sleeve and retractor.

Accordingly, an object of the present invention is to provide a new and improved remotely manipulated retractor for use during surgical procedures carried out at least in part via trocar sleeves. Another object is to provide a surgical retractor which does not excessively obstruct the vision or movements of a surgeon while he is manipulating tools which are inserted into a human body through a trocar sleeve.

Yet another object of the invention is to provide a retractor which may be sanitized quickly and easily. Here an object is to provide a retractor which may be placed in and sterilized by an autoclave.

Yet another object of the invention is to provide a retractor which is very light weight and yet meets the other requirements for surgery.

A preferred embodiment of the invention is seen in the attached drawings, in which.

Figure 3:
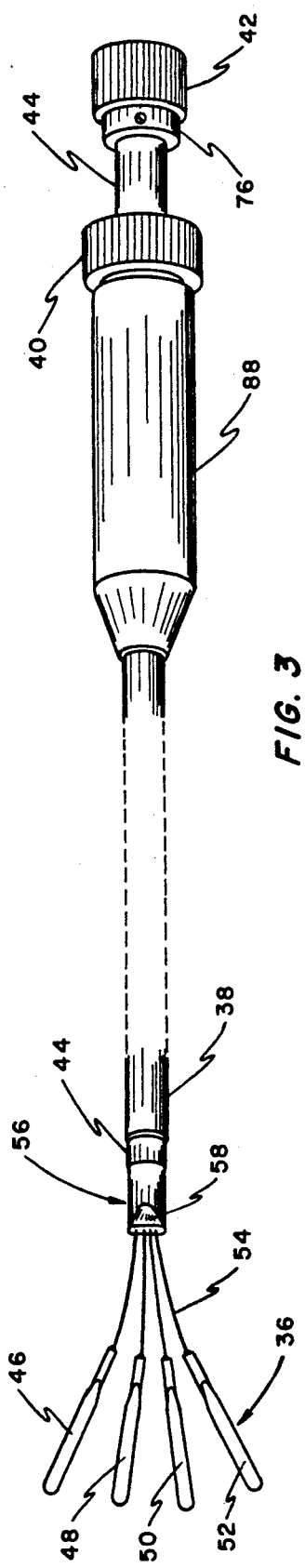
FIG. 3 is a perspective view of the inventive retractor.

FIGS. 4A-D together provide an exploded view of certain internal parts of the retractor of FIG. 6;

FIG. 5 is a cross-sectional view, taken along line 5—5 of FIGS. 4B and 4C with the parts of those FIGS. assembled;

FIG. 6 is an exploded view of external parts of the retractor of FIG. 3; and

FIG. 7 is an end view of the retractor of FIG. 3 with the retractor fingers inside the retractor tube.

Figure 1:
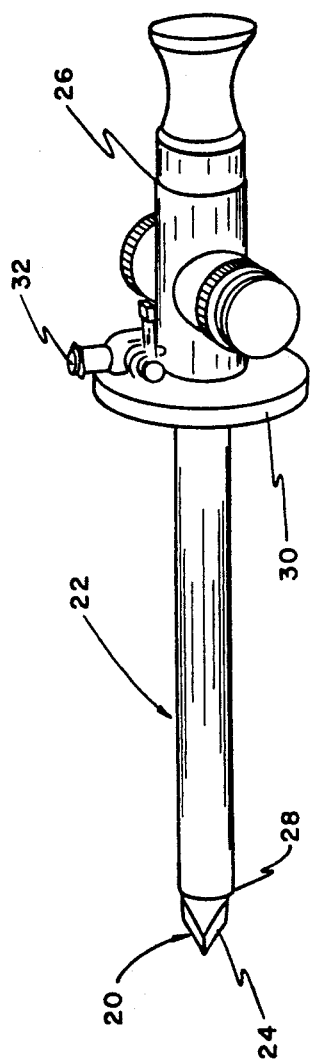
FIG. 1 is a perspective view of an assembled trocar and a trocar sleeve.

FIG. 1 shows an assembled combination of trocar 20 and trocar sleeve 22 which are used to make a puncture wound in a human body. The trocar 20 is a device having a knife blade 24 and a handle 26 which slides into a relatively long cylindrical tube 28. When the trocar 20 is pressed into an abdominal wall, for example, blade 24 make a puncture wound. Depending upon the operation, the trocar sleeve 28 may be pushed into the body until it is stopped by a collar 30 attached to the end of the tube 28. (This collar is optional and may often be omitted from the sleeve 22). The trocar 20 and sleeve 22 may have any well known form. In this case, it has a gas port 32 which enables $CO_2$ to be pumped into the body in order to expand it so that there will be enough internal room to perform an operation.

Figure 2:
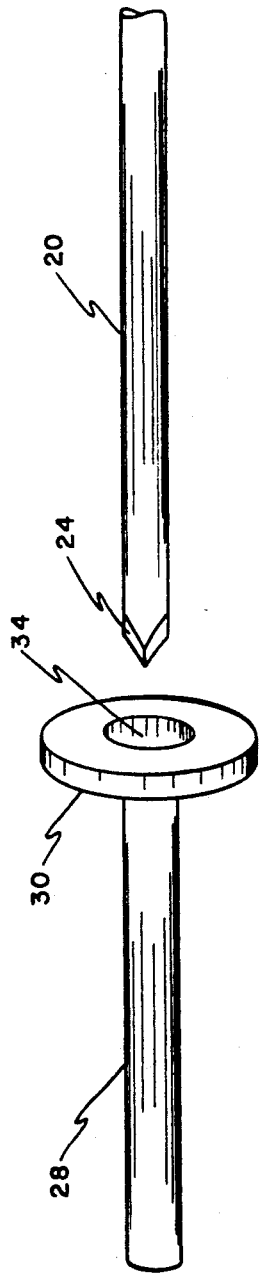
FIG. 2 is a fragment of FIG. 1 with the trocar removed from the trocar sleeve.

Once in place, the trocar 20 is pulled form the sleeve 28, leaving a hole 34 (FIG. 2) which may receive the inventive retractor, a laparoscope, surgical instruments, or the like. A seal may be provided at the entrance of hole 34 to prevent the $CO_2$ gas from escaping from the abdomen.

The inventive retractor is seen in FIGS. 3-7. The retractor (FIG. 3) comprises a plurality (here four) of fingers 36 in a fan-like orientation, a long outer retractor tube 38 having an outside diameter which slips easily into a hole 34 (FIG. 2) and through the trocar sleeve, a locking nut 40, and a control knob 42. The control knob 42 is attached to the proximal end and the fingers 36 are attached to the distal end of an inner retractor tube 44 which telescopes and slides easily into, through, or out of the tube 38. When the telescoping inner and outer retractor tubes 44 and 38 are in a desired position relative to each other, the locking nut 40 is tightened to make them immovable relative to each other.

The fingers 36 comprise four small plates 46-52 each about an inch long, an eighth of a inch wide, and a thirty-second of an inch thick. Each finger is affixed to the end of a wire spring such as 54. The wire springs are stiff enough to enable the fingers to perform their retracting function and yet resilient enough not to damage the human tissue which is being pressed down or pulled aside. On one end, the springs 54 may be affixed on to individually associated ones of the fingers 36 and, on the other end, to a solid block of metal 56 pivotally coupled to the distal end of the inner retractor tube 44.

The means for articulating of the fingers 36 at the distal end of inner retractor tube 44 is best seen in FIGS. 4A-4D, which are rotated by 90° relative to the view of FIG. 3. The metal block 56 has sides tapered at 58, 58 to facilitate moving through the puncture wound and between tissue inside the abdomen without simultaneously punching or snagging it. The back end of metal block 56 has a tongue 59 which pivots on a hinge pin 60 affixed to the end 62 of the inner retractor tube 44. Hence, the metal block 56 and fingers 46-52 have a freedom to move back and forth in directions A-B as it pivots on pin 60.

A rod or pull wire 64 is pivotally attached at 66 to the metal block 56 in order to control the attitude of the block and fingers by moving back and forth in directions C, D. The rod or pull wire 64 extends from the distal end through the entire length to the proximal end of the inner retractor tube 44. At the proximal end, the rod or pull wire 64 is permanently attached in a hole 68 of a sliding housing 70 (FIG. 4B). Therefore, if housing 70 slides in direction C, the block 56 and fingers 46-52 move in direction A. If the housing 70 slides in direction D, the metal block 56 and fingers 46-52 move in direction B.

The equipment for controlling the position of housing 70 (FIG. 4D) includes a knob 42 having a threaded shaft 74 integral therewith. A bushing or collar 76 fits over and is rotatably attached to the inner retractor tube 44. Collar 76 is rigidly held in place on knob 42 by any suitable means, such as solder or set screw 78. Hence, the control knob 42 is free to rotate but is not free to move longitudinally with respect to the inner retractor tube 44.

A slotted guide 80 (FIG. 4C) has a hole 82 through which the shaft 74 of control knob 42 may pass. The guide 80 has two arms 84, 86 which are shaped and dimensioned to slidingly receive and embrace the housing 70. (In FIG. 4B, housing 70 is seen rotated by 9020 relative to the position of arms 84, 86 as shown in FIG. 4C, in order to show hole 68 and arms 84, 96. FIG. 5 shows the actual assembled orientation of housing 70 and slotted guide 80.) Housing 70 has a threaded hole 71 into which the shaft 74 may turn. Therefore, if knob 42 is turned in one direction housing 70 slides in direction C. If the know 42 is turned in an opposite direction, housing 70 slides in direction D.

FIG. 6 shows the mechanism for immobilizing and locking the inner and outer retractor tubes 44, 38 relative to each other. To clearly reveal all parts, the inner tube 44 is shown intermittently throughout FIG. 6; however, it should be understood that it is a continuous tube. The proximal end of the outer tube 38 is attached to an outer chuck piece 88 having a passageway 90 through which the inner tube 44 passes. An inner chuck piece 92 has two or four oppositely disposed slots 94, 94 which form jaws 96, 98 that may be squeezed together to grip inner retractor tube 44 or relaxed to release the grip. The front end of the jaws 96, 98 are tapered so that they may be squeezed together by being driven into a complementary taper 100 at the bottom at hole 102 or released by retraction of inner chuck piece 92 from the tapered bottom of hole 102.

A threaded locking nut or cap 40 fits onto threads 104 on the outer chuck 88. Thus, when locking nut or cap 40 is tightened, the jaws of inner chuck part 92 are squeezed together to lock the telescoping tubes 38, 44 relative to each other. When the cap 40 is loosened, the resilient of the member 92 acting upon tapered surface 100, causes the inner chuck part to back off, thus loosening the inner retractor tube 44 from the outer retractor tube 38.

To assemble the parts shown in FIG. 6, the inner retractor tube 44 is extended through a hole 106 in inner chuck part 92 and then through passageway 90 in outer tube 38. The locking nut or cap 40 is fitted onto and threaded over threaded end 104 of the outer chuck 88. Thus, the two tubes 38, 44 are locked together when cap 40 is tightened and released from each other when the cap is loosened.

FIG. 7 is an end view of the retractor when the inner retractor tube 44 is being inserted into or withdrawn from the outer retractor tube 38. The angles of the wire springs 54 are such that the four fingers 46-52 automatically come together into a compressed and stacked condition.

Those who are skilled in the art will readily perceive how to modify the invention. Therefore, the appended claims are to be construed to cover all equivalent structures which fall within the true scope and spirit of the invention.

I claim:

1. A retractor for use during surgical procedures conducted through trocar sleeves, said retractor comprising telescoping inner and outer retractor tubes, a plurality of fingers pivotally attached to a distal end of one of said tubes, and means on a proximal end of said tubes for selectively controlling the pivotal attitude of said fingers, a block which is pivotally attached to said distal end of said inner tube, said fingers being attached to said block, a pull wire pivotally attached to said block in order to control the attitude thereof, said pull wire extending throughout the length of said inner retractor tube, and means at the proximal end of said inner tube for pulling or pushing said pull wire.

2. The retractor of claim 1 wherein each of said fingers is attached to said distal end by individually associated wire springs, said wire springs being shaped to cause said fingers to come together in a compressed and stacked condition when said fingers are inserted through or withdrawn into said outer tube.

3. The retractor of claim 1 and means for selectively interlocking and longitudinally immobilizing said inner and outer tubes when said fingers are properly positioned at the distal end of said outer tube.

4. The retractor of claim 1 wherein said fingers are attached to a block at the distal end of said inner retractor tube, said block being tapered to facilitate the movement through body tissue.

5. The retractor of claim 1 wherein said means at said proximal end for pulling or pushing said pull wire comprises a housing attached to said pull wire and mounted for longitudinal movement within said inner retractor tube, and means for selectively moving said housing along said longitudinal movement.

6. The retractor of claim 5 wherein said means for selectively moving said housing comprises a threaded shaft fitted into a threaded hole in said housing whereby a rotation of said threaded shaft moves said housing.

7. An elongated retractor for use during surgical procedures performed through a trocar sleeve, said elongated retractor having a plurality of fingers extending from a distal end of said retractor, said fingers spreading apart when extended from said distal end, means for pivotally enabling said extended and spread apart fingers to articulate over an approximate range of 180° to 90° relative to the elongated direction of said retractor, a pivot point for said articulation being located at the distal end of said retractor, means responsive to a control function performed at a proximal end of said retractor for articulating said extended and spread apart fingers, and means extending along a length of said retractor for articulating said fingers responsive to said control function performed at said proximal end.

8. The retractor of claim 7 wherein said spreading of said fingers produces a fan shape when in an operative position and for compressing the position of said fingers to fit into a minimum envelope when said retractor is in said trocar sleeve.

9. The retractor of claim 7 wherein said pivoting means is a block at said distal end of said retractor, said fingers are approximately one inch long, an eighth of an inch wide, and a thirty-second of an inch thick, each of said fingers being attached to said block via an individually associated wire spring, said wire springs having a shape which spreads said fingers into a fan-like shape when extended from said distal end and which compresses the positions of said fingers when confined within said retractor.

10. An elongated device for controlling the position of human tissue during surgery, said device comprising means for selectively spreading a retracting means into a fan shape, means for articulating said fan shape to a selected position between an approximation of an extension of said elongation and a right angle relative to said elongation, means for locking said retracing means in said selected position, and means for compressing said fan shape into a compact configuration for movement into and out of an operative position.

* * * * *